US00PP18388P3

(12) United States Plant Patent
Larsen

(10) Patent No.: US PP18,388 P3
(45) Date of Patent: Jan. 1, 2008

(54) ***OSTEOSPERMUM* PLANT NAMED 'SUNNY DAVINA'**

(50) Latin Name: *Osteospermum ecklonis*
Varietal Denomination: Sunny Davina

(75) Inventor: Bjame N. Larsen, Odense (DK)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/412,504

(22) Filed: Apr. 27, 2006

(65) Prior Publication Data

US 2006/0282927 P1 Dec. 14, 2006

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
*Assistant Examiner*—Annette H Para

(57) ABSTRACT

A new and distinct cultivar of *osteospermum* plant named Sunny Davina, particularly characterized by its ray-floret color, in which the upper surface of mature ray florets having alternate stripes of a darker and a lighter purple, upright growth habit, elliptic ray florets in one or two complete whorls, and by its nonvariegated leaves.

1 Drawing Sheet

The present invention relates to a new and distinct cultivar of *Osteospermum* plant, botanically known as *Osteospermum ecklonis,* and referred to by the varietal denomination 'Sunny Davina'.

The new cultivar is the product of a planned breeding program carried out by the inventor is Odense, Denmark. The objective of the breeding program was to create new *osteospermum* cultivars with distinctly new inflorescence colors.

The new cultivar originated from a cross made by the inventor in Odense, Denmark, in May 2002. The female or seed parent was the cultivar 'Sunny Serena', disclosed in U.S. Plant Pat. No. 15,693, and primarily characterized by its compact, upright, mounded-plant habit, its dense and bushy growth habit, its freely flowering habit, and its pale yellow ray florets and contrasting grey disc florets. The male or pollen parent was an unnamed and unpatented proprietary seedling identified by the code number 30.013.01. The characteristics of the male parent are not presently available.

The first act of asexual reproduction of the new cultivar was accomplished when vegetative cuttings were made from the selection in April 2004 in a controlled environment in Odense, Denmark, by or under the supervision of the inventor.

The new cultivar has not been observed under all possible environmental conditions. The phenotype may vary significantly with variations in environment, such as temperature, light intensity, and day length without, however, any variance in genotype.

SUMMARY OF THE INVENTION

The following traits have been repeatedly observed and have been determined to be basic characteristics of the new cultivar, which, in combination, distinguish the new cultivar as being new and distinct:

1. The new cultivar has an upright growing habit, and possesses many of the growth characteristics of the female parent, 'Sunny Serena'.
2. Nonvariegated leaves.

3. Elliptic ray florets formed in one or two complete ray floret whorls.
4. The ray-floret color is unique, with the upper surfaces of the ray florets having alternate stripes of a darker purple (78A) and a lighter purple (78B), creating a very interesting effect.

Of the many commercial cultivars known to the present inventor(s), the most similar cultivar in comparison to the new cultivar is the female parent, 'Sunny Serena'. The primary distinction is in ray floret color, with the color of the upper side of the ray florets of 'Sunny Serena' being a solid, pale orange (RHS 19D).

BRIEF DESCRIPTION OF THE PHOTOGRAPHS

The photograph at the bottom of the sheet shows a front perspective view of typical flowering plants (three) of the new cultivar. The photograph at the top of the sheet is a view showing in more detail the inflorescences of the new cultivar, particularly the novel striping on the upper surface of the ray florets.

The colors in the photographs are as true as is reasonably possible with colored reproductions of this type. If any difference exist between the photographic color and the color values described below, the values in the detailed description are accurate.

DETAILED BOTANICAL DESCRIPTION

In the following description, color references are made to The Royal Horticultural Society Colour Chart. The values are based on plant material grown in Bonsall, Calif., with the plants' being approximately 16 weeks old.

Botanical classification: *Osteospermum ecklonis* cv 'Sunny Davina'.

*Parentage.*—Female parent: 'Sunny Serena'.

*Pollen parent.*—A proprietary cultivar identified as 30.013.01.

Propagation:

*Type.*—Terminal vegetative cuttings.

*Time to initiate roots.*—About 10 to 14 days at 18–20 degrees C.

*Root description.*—Fine, fibrous, and branching.

Plant description:

*General appearance and shape.*—Oval; very upright.

*Habit.*—Loose, open, rounded canopy is uniform; excellent vigor and very free-branching.

*Plant height.*—42 cm.

*Plant diameter or area of spread.*—47–50 cm.

*Lateral branching.*—Number of primary lateral branches: 4. Number of secondary lateral branches: 6–7. Length of primary branches: About 34 cm. to 38 cm. Diameter: About 0.45 cm. to 6.0 cm. Internode length: About 1.3 cm. to 1.8 cm.

*Texture.*—Smooth, glabrous.

*Color.*—145A.

*Foliage.*—Arrangement: Alternate. Simple or Compound: Simple. Length: About 5.6 cm. to 6.0 cm. Width: About 3.0 cm. to 3.5 cm., becoming smaller toward tip. Shape: Oblanceolate to obovate. Apex shape: Broadly acute. Base shape: Attenuate. Margin: Nearly entire but having irregular points. Texture: Top is slightly course, and bottom is minutely pubescent. Color: Developing foliage: Upper surface, 147A. Lower surface, 147B. Mature foliage: Upper surface, 147A. Lower surface, 147B. Venation, upper and lower surfaces: 147B. Petiole: Length, 1.0 cm. to 1.6 cm. Diameter, 0.3 cm. Color: Both upper and lower sections, 144A. Other foliage characteristics: Dominant midvein, then arcuate to reticulate; no distinct petiole.

Inflorescence:

*Appearance.*—Solitary, terminal, and axillary.

*Form.*—Single daisy; actinomorphic.

*Orientation.*—Upright if terminal. Outward if axillary.

*Longevity.*—5–6 days.

*Fragrance.*—None.

*Quantity.*—About 8 open inflorescences and 20 visible buds on main stem, 3–5 inflorescences and 8 buds on lateral stems.

*Size.*—Total diameter: 7.5 cm. Depth: About 2.0 cm. Diameter of disc: 1.3 cm. Receptacle diameter: 2.0 cm. Receptacle height: 1.1 cm.

*Buds* (*just before anthesis*).—Height: 2.4 cm. Diameter: 1.3 cm. Shape: Ovoid. Color: Greyer than 79D.

*Ray florets.*—Quantity per inflorescence: 23. Shape: Ligulate. Length: 3.9 cm. Width: 0.9 cm. Apex: Nearly round and minutely tridentate. Base: Acute. Margin: Entire. Texture: Smooth. Aspect: Not completely flat, about 75 degrees from vertical. Color: When opening: Upper surface, 88C. Lower surface, 88D, with narrow stripes of 88A, and tips overlaid with 144B. Mature: Upper surface: Alternating stripes of 78A and 78B. Lower surface: Ground color is greyer than 77A, with thin stripes of 79A.

*Disc florets.*—Quantity per inflorescence: Approximately 90. Shape: Tubular. Apex: Acute, 5 points. Base: Fused into short tube. Length: 0.9 cm. Width: 0.2 cm at apex. 0.1 cm at base. Color: Immature, 79A. Mature, 79D.

*Involucral bracts.*—Quantity per flower: 18. Length: 1.2 cm. Width: 0.2 cm. Shape: Lanceolate. Apex: Acute. Base: Truncate. Color: Upper surface, 144B. Lower surface: 144A.

*Peduncles.*—Strength: Good. Aspect: Upright to angle of 30 degrees from vertical. Length: Terminal peduncle, 9.5 cm. Fourth peduncle, 3.0 cm. Diameter: About 0.2 cm. Texture: Minutely pubescent. Color: 144B.

*Reproductive organs.*—Androecium: Stamens in disc florets. Stamen number: 5. Anther shape and length: Oblong; 0.25 cm. Anther color: 21B. Gynoecium: On ray florets only. Pistil length: 0.6 cm. Stigma shape: Bipartite. Stigma color: 79B. Style length: 0.4 cm. Style color: 83D. Seed/fruit: None observed.

Other inflorescence characteristics: Inflorescences close at night. Immature discs are dark violet but mature to a lighter, greyed violet. When bright orange pollen is shed, discs develop a bull's-eye ring. Sunny Davina is very floriferous with excellent branching.

I claim:

1. A new and distinct cultivar of *osteospermum* plant named Sunny Davina, as illustrated and described.

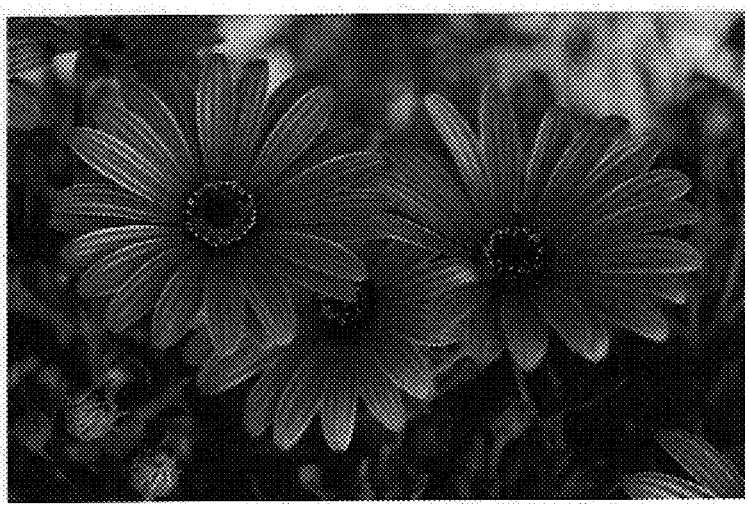
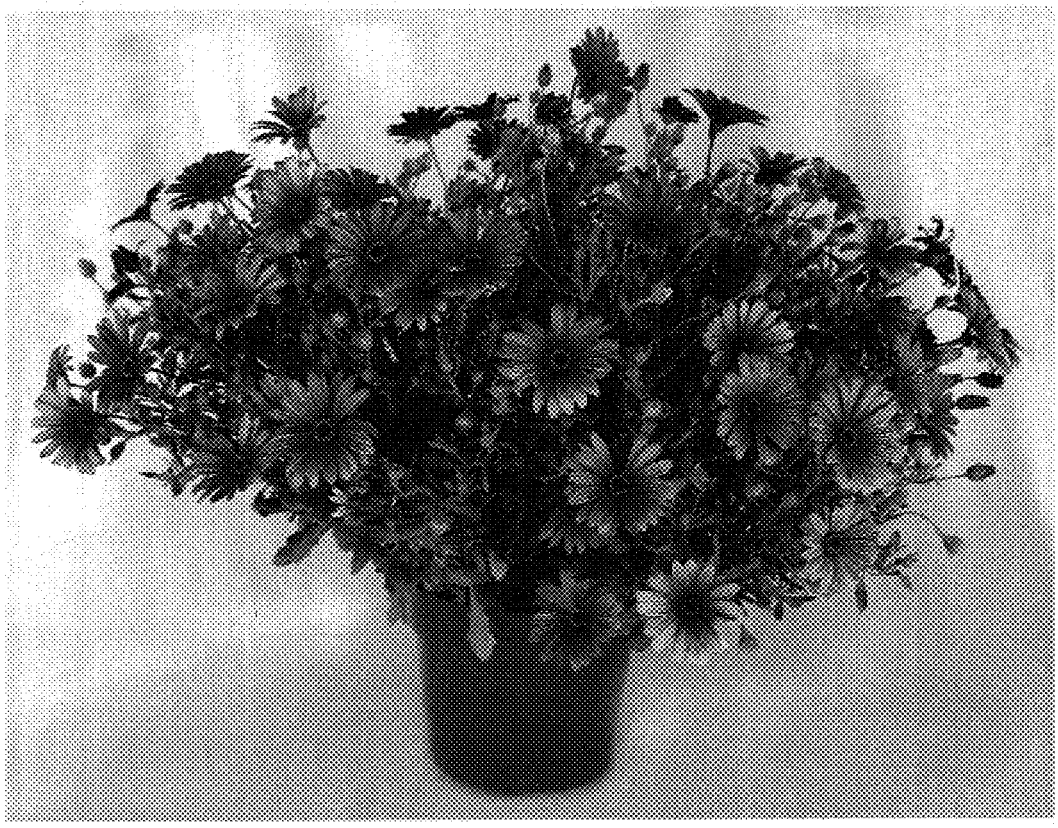

* * * * *